United States Patent
Damian et al.

(10) Patent No.: US 11,203,632 B2
(45) Date of Patent: Dec. 21, 2021

(54) ANTIBODY VARIANTS

(71) Applicant: GlaxoSmithKline Intellectual Property Development Limited, Brentford (GB)

(72) Inventors: Valeriu Damian, King of Prussia, PA (US); Austin Keith Doyle, Stevenage (GB); Laura Maria Halo, Stevenage (GB); Emma R. Harding, Stevenage (GB); Xuan Hong, King of Prussia, PA (US); Alan Peter Lewis, Stevenage (GB); Mark Uden, Stevenage (GB)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 162 days.

(21) Appl. No.: 15/749,210

(22) PCT Filed: Jul. 29, 2016

(86) PCT No.: PCT/EP2016/068127
§ 371 (c)(1),
(2) Date: Jan. 31, 2018

(87) PCT Pub. No.: WO2017/021294
PCT Pub. Date: Feb. 9, 2017

(65) Prior Publication Data
US 2018/0222964 A1    Aug. 9, 2018

Related U.S. Application Data

(60) Provisional application No. 62/199,346, filed on Jul. 31, 2015.

(51) Int. Cl.
C40B 30/04 (2006.01)
C07K 16/00 (2006.01)
A61K 39/00 (2006.01)

(52) U.S. Cl.
CPC .......... *C07K 16/00* (2013.01); *A61K 2039/54* (2013.01); *C07K 2317/567* (2013.01); *C07K 2317/94* (2013.01); *C40B 30/04* (2013.01)

(58) Field of Classification Search
None
See application file for complete search history.

(56) References Cited

U.S. PATENT DOCUMENTS

2011/0076275 A1   3/2011  Igawa et al.

FOREIGN PATENT DOCUMENTS

EP        2006381 A1     12/2008
JP     2013216660 A      10/2013
(Continued)

OTHER PUBLICATIONS

Fathallah et al., "Anatomical, physiological and experimental factors affecting the bioavailability of sc administered large biotherapeutics", *Journal of Pharmaceutical Sciences*, vol. 104, No. 2, pp. 301-306 (2015).

(Continued)

*Primary Examiner* — Christian C Boesen
(74) *Attorney, Agent, or Firm* — Shan Liu; Scott Young

(57) ABSTRACT

The present invention relates to methods of selecting, screening, engineering, making and modifying antibodies that have improved bioavailability upon subcutaneous administration to a human. Antibodies and variant antibodies with improved bioavailability upon subcutaneous administration to a human are also described.

7 Claims, 7 Drawing Sheets

(56) References Cited

FOREIGN PATENT DOCUMENTS

Figure 1:
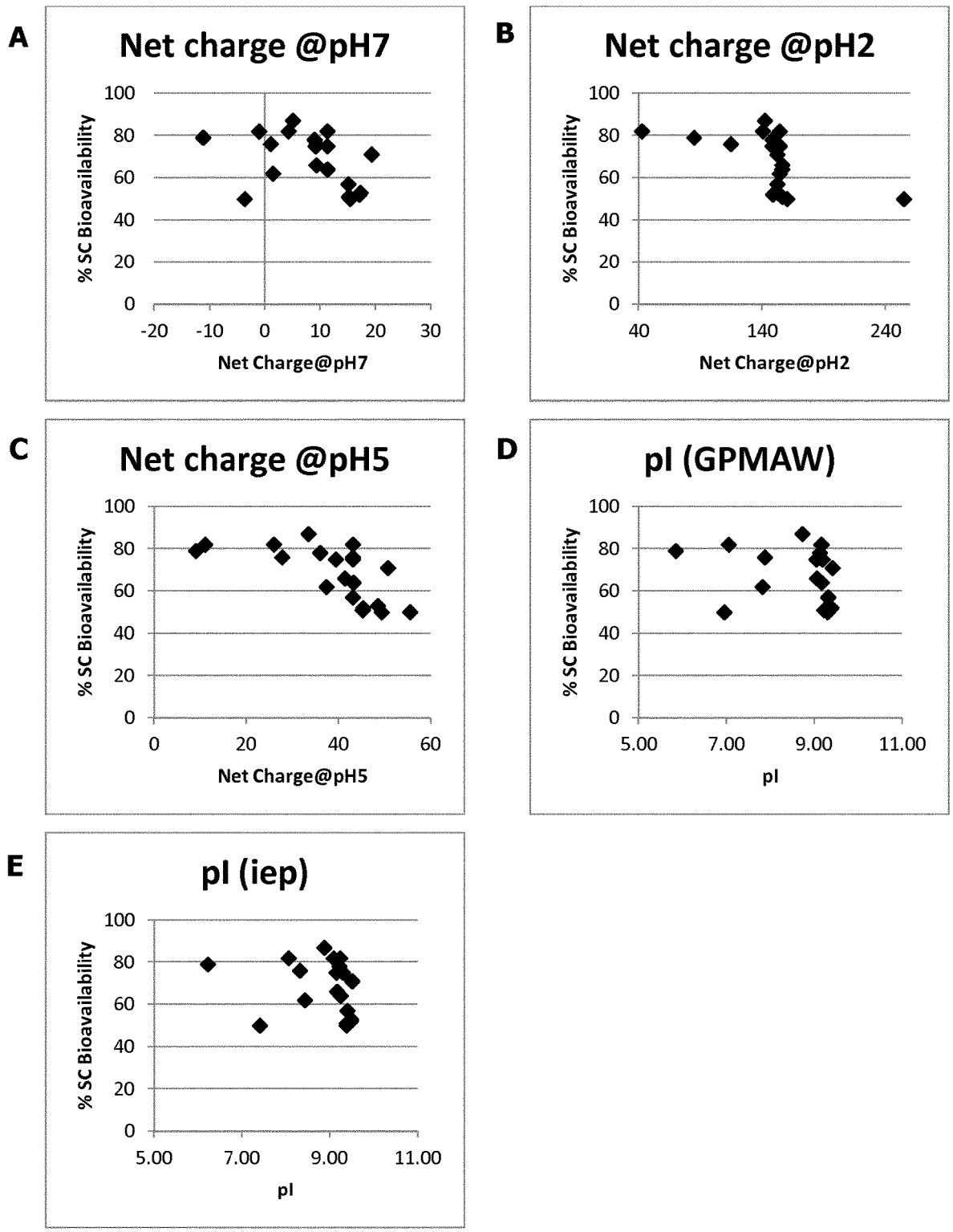

| JP | 2014057582 A | 4/2014 |
|---|---|---|
| JP | 2015517490 A | 6/2015 |
| WO | 2007114319 A1 | 10/2007 |
| WO | WO 2011/149999 A2 | 12/2011 |
| WO | WO 2012/065072 A2 | 5/2012 |

OTHER PUBLICATIONS

Hong et al., "Enhanced Cellular Uptake and Transport of Polyclonal Immunoglobulin G and Fab After Their Cationization", *Journal of Drug Targeting, Harwood Academic Publishers GMBH, DE*, vol. 8, No. 2, pp. 67-77 (2000).

Igawa et al., "Reduced elimination of IgG antibodies by engineering the variable region", *Protein Engineering Design and Selection*, vol. 23, No. 5, pp. 385-392 (2010).

Zheng et al., "Minipig as a potential translatable model for monoclonal antibody pharmacokinetics after intravenous and subcutaneous administration", *mAbs*, vol. 4, No. 2, pp. 243-255 (2012).

ANTIBODY VARIANTS

This application is a § 371 application of International Application No. PCT/EP2016/068127, filed 29 Jul. 2016, which claims the benefit of U.S. Provisional Application No. 62/199,346, filed 31 Jul. 2015, both of which are incorporated herein in their entirety.

FIELD OF THE INVENTION

The present invention relates to methods of selecting, screening, engineering, making and modifying antibodies that have improved bioavailability upon subcutaneous administration to a human. Antibodies and variant antibodies with improved bioavailability upon subcutaneous administration to a human are also described.

BACKGROUND TO THE INVENTION

Subcutaneous (SC) administration of an antibody drug product involves administration into the extracellular space of the subcutaneous tissue (hypodermis). SC administration has many advantages such as self-administration, improved patient compliance, and decreased health care costs. Once administered, antibody drug products use a variety of mechanisms of action. Despite the prevalence of the SC route of administration, there is still little understanding of bioavailability of antibodies upon administration. Bioavailability (BA) is the percentage of drug that reaches the systemic circulation and is influenced by the relative rates of pre-systemic catabolism and systemic absorption. Pathways for systemic absorption include indirect transport through lymphatic vessels to the blood, and direct transport via diffusion into blood vessels around the site of injection. It generally takes 2 to 8 days for subcutaneously administered antibodies to reach the peak plasma concentration. The BA of antibodies typically ranges between 40-85%.

Thus, BA affects the total amount of antibody drug product required to be administered, which therefore influences the cost of goods. With the limited volume that can be delivered subcutaneously (1-1.5 ml), and concentrations limited by viscosity and aggregation propensity, improving BA can increase the effective dose that is administered.

However, there is currently no way of accurately predicting the BA of an antibody drug product prior to human clinical trials. Pre-clinical animal models such as rodents, *Cynomolgus* monkeys, and Göttingen minipigs are not always reliably predictive of human BA.

Therefore, there is a need in the art to predict the bioavailability of an antibody drug product upon subcutaneous administration in a human subject.

SUMMARY OF THE INVENTION

According to a first aspect of the invention, there is provided a method of selecting an antibody comprising: (a) producing two or more antibodies to the same antigen; and (b) selecting the antibody sequence which has:

(i) a net charge at about pH7 that is closer to +5, or a pI that is closer to 8.8; and/or (ii) a net charge of between 0 and +12 at about pH7, or a pI of between 8.4 and 9.3; wherein the antibody selected has a higher bioavailability.

According to a further aspect of the invention, there is provided a method of making an antibody which comprises selecting and combining two or more human germline framework amino acid sequences, regions, or amino acids, to generate an antibody which has: a net charge of between 0 and +12 at about pH7, or a pI of between 8.4 and 9.3; wherein the antibody generated has a higher bioavailability.

According to a further aspect of the invention, there is provided a method of improving the bioavailability of an antibody, comprising modifying the amino acid sequence of the antibody to result in: a net charge of between 0 and +12 at about pH7, or a pI of between 8.4 and 9.3.

According to a further aspect of the invention, there is provided a method of predicting the bioavailability of an antibody using net charge at about pH7 or pI, wherein an improved bioavailability is correlated with a net charge of between 0 and +12 at about pH7, or a pI of between 8.4 and 9.3.

According to a further aspect of the invention, there is provided a method of making an antibody sequence library, wherein the library is engineered to comprise antibodies having a net charge of between 0 and +12 at about pH7, or a pI of between 8.4 and 9.3; wherein an antibody derived from the library has a bioavailability of at least 60%.

According to a further aspect of the invention, there is provided an antibody resulting from any one of the methods described.

According to a further aspect of the invention, there is provided a variant of a parent antibody sequence, wherein the variant comprises combining two or more human germline framework sequences, regions, or amino acids to generate a variant antibody having: (i) a net charge at about pH7 that is closer to +5, or a pI that is closer to 8.8 than the parent antibody; and/or (ii) a net charge of between 0 and +12 at about pH7, or a pI of between 8.4 and 9.3 compared with the parent antibody; wherein the variant antibody has a higher bioavailability than the parent antibody.

According to a further aspect of the invention, there is provided a method for subcutaneous administration of an antibody to a human, comprising administering the antibody as described herein or the variant as described herein to a patient in need thereof.

According to a further aspect of the invention, there is provided an antibody sequence library, wherein the library is engineered to comprise antibodies having a net charge of between 0 and +12 at about pH7, or a pI of between 8.4 and 9.3.

DESCRIPTION OF DRAWINGS/FIGURES

FIG. 1: Relationship between human subcutaneous bioavailability and either net charge at pH 7 (FIG. 1A), at pH2 (FIG. 1B), at pH5 (Figure C); or pI calculated using GPMAW mean (FIG. 1D) or iep (FIG. 1E) for abatacept, etanercept, rilonacept, certolizumab, denosumab, tralokinumab, omalizumab, rituximab, trastuzumab, mAb1, belimumab, mAb2, mAb3, canakinumab, adalimumab, ustekinumab, tocilizumab, mAb4, golimumab, and efalizumab, based on Table 4.

Figure 2:
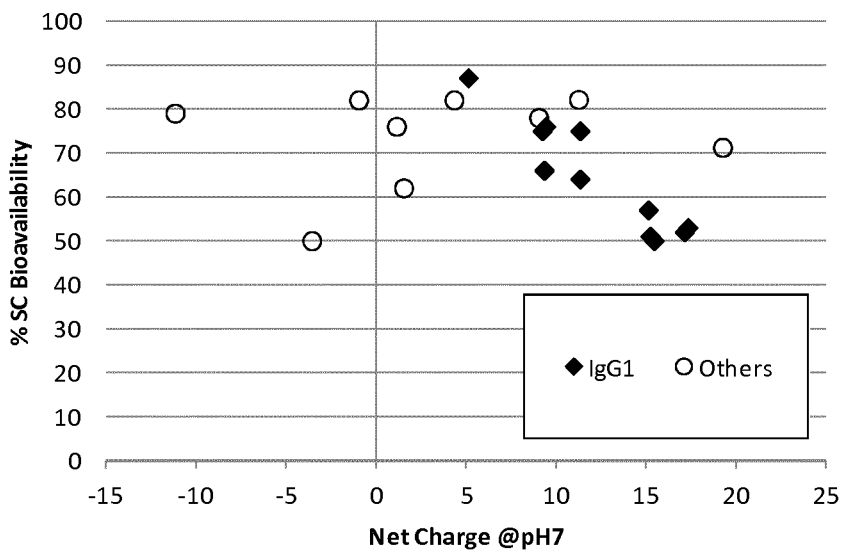
Figure 2:
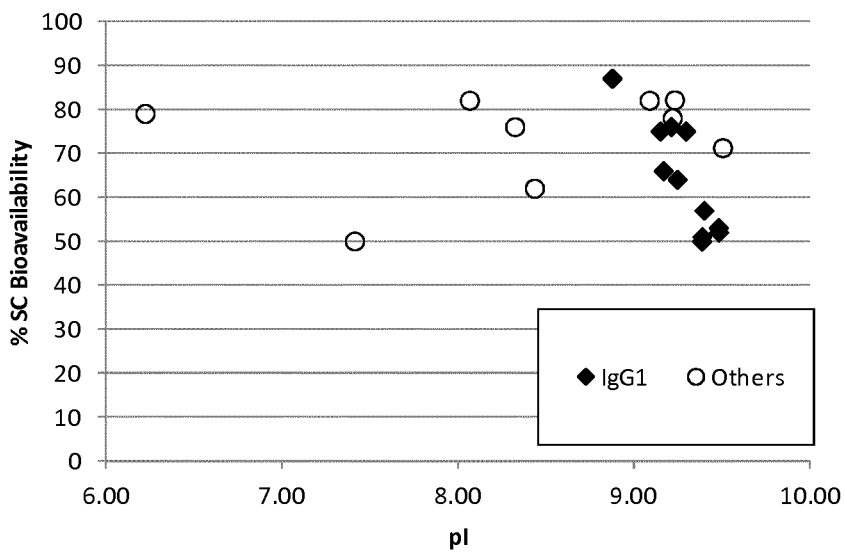

FIG. 2: Relationship between bioavailability and either net charge at pH7 (FIG. 2A) or pI (iep) (FIG. 2B), highlighting the differences between IgG1 and "others": IgG1 includes: mAb1, belimumab, mAb2, mAb3, canakinumab, adalimumab, ustekinumab, tocilizumab, mAb4, golimumab, and efalizumab; "others" include abtacept, etanercept, rilonacept, certolizumab, denosumab, tralokinumab, omalizumab, rituximab and trastuzumab.

Figure 3:
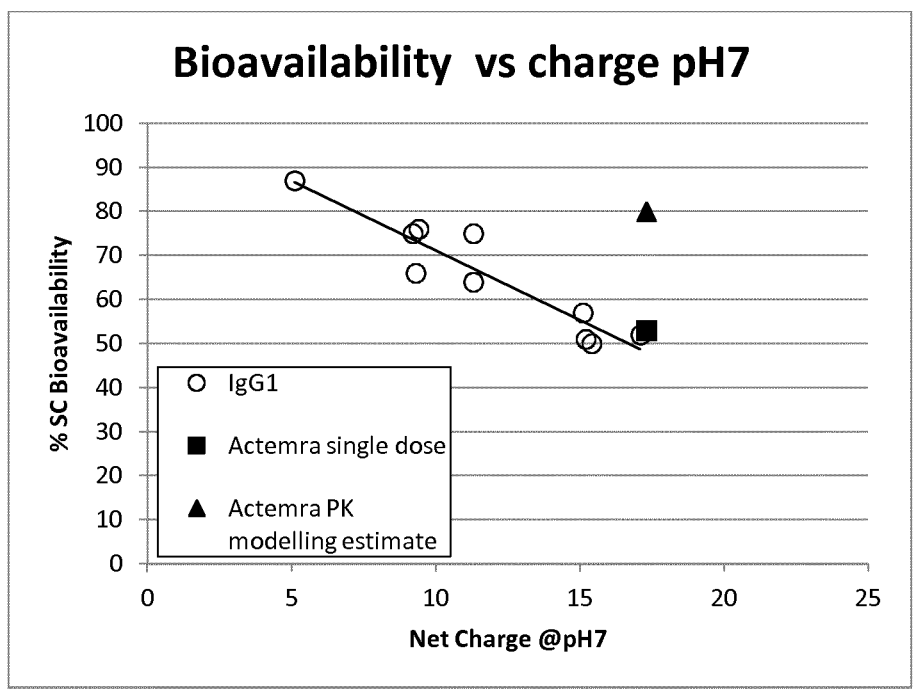

FIG. 3: Relationship of BA values of Actemra and "IgG1" (mAb1, belimumab, mAb2, mAb3, canakinumab, adalimumab, ustekinumab, tocilizumab, mAb4, golimumab, and efalizumab) compared with net charge at pH7.

Figure 4:
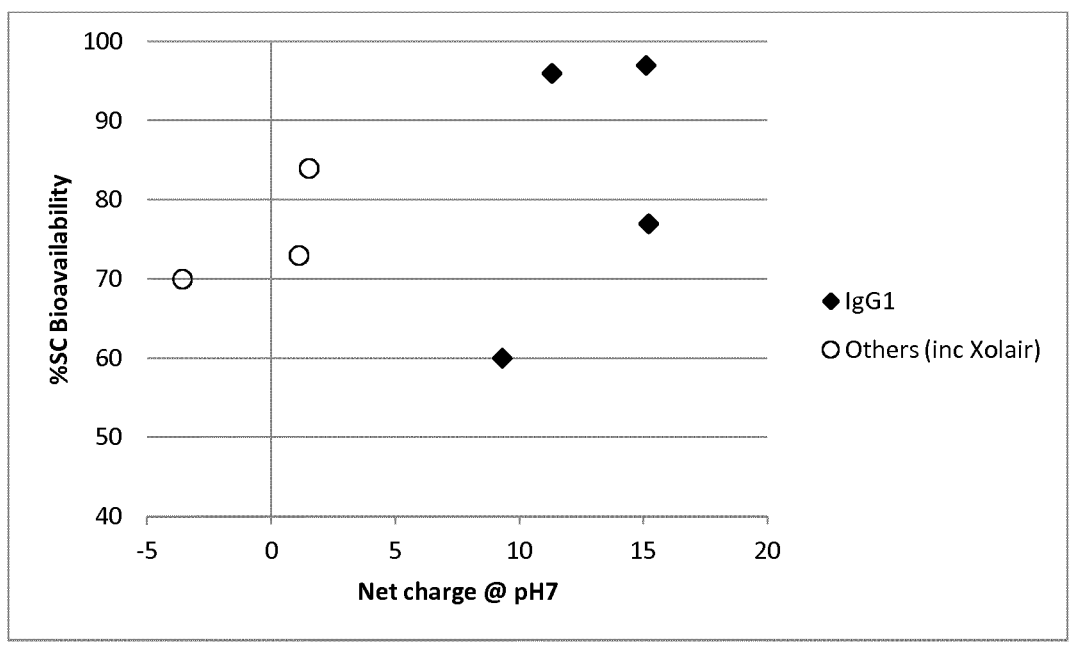

FIG. 4: Relationship of *Cynomolgus* monkey bioavailability data with net charge at pH7 for four IgGs: Canakinumab, Adalimumab, Golimumab, Ustekinumab; and "others" Etanercept, Rilanocept, and Omalizumab.

Figure 5:
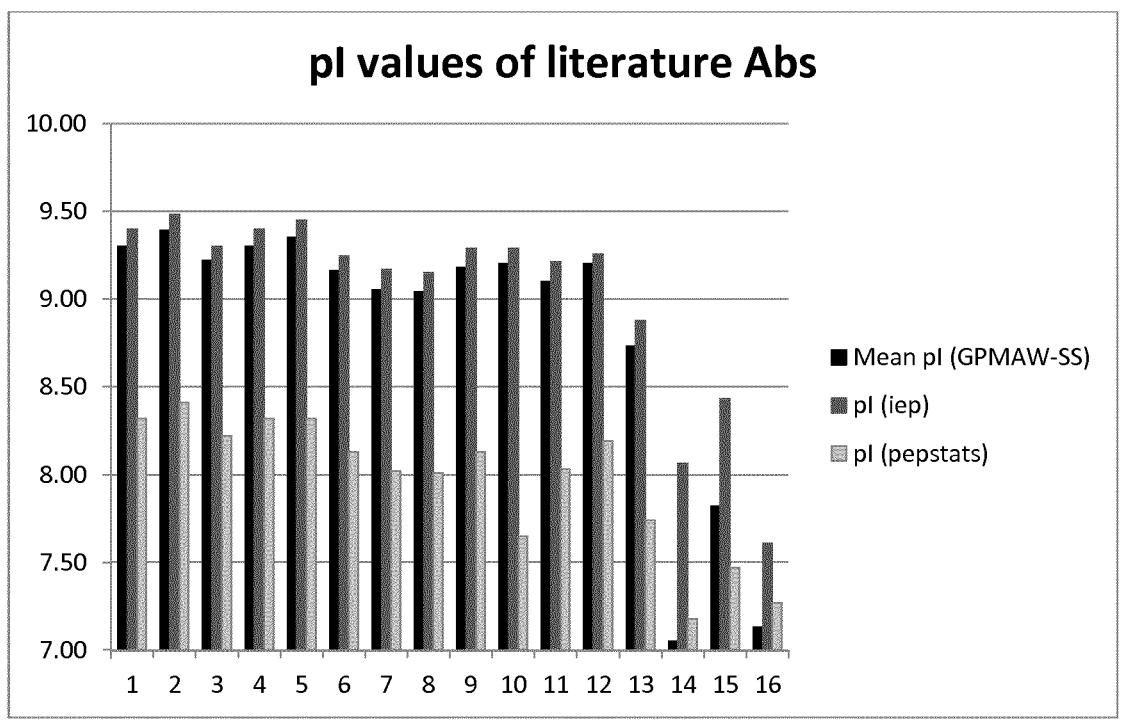

FIG. 5: Comparison of pI values of certolizumab, trastuzumab, tralokinumab, abtacept, denosumab, beliumumab, etanercept, rituximab, canakinumab, adalimumab, omalizumab, ustekinumab, tocilizumab, golimumab, efalizumab, and rilonacept calculated using GPMAW, pepstats and iep.

Figure 6:
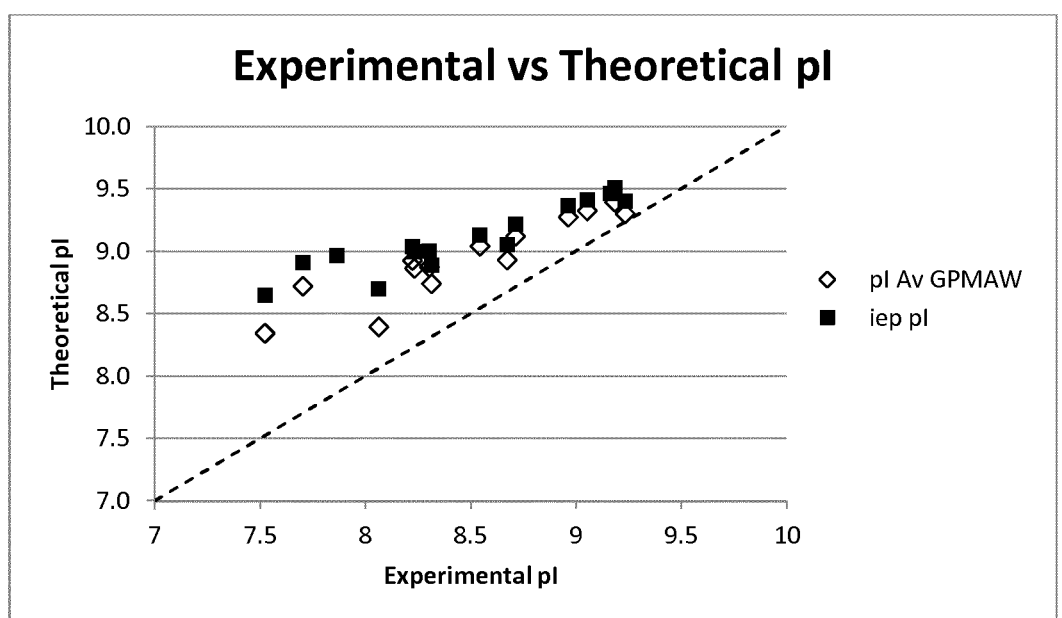

FIG. 6: Comparison of experimental pI values and computational pI values calculated by GPMAW for in-house mAbs 2, 5 to 23, based on Table 6.

Figure 7:
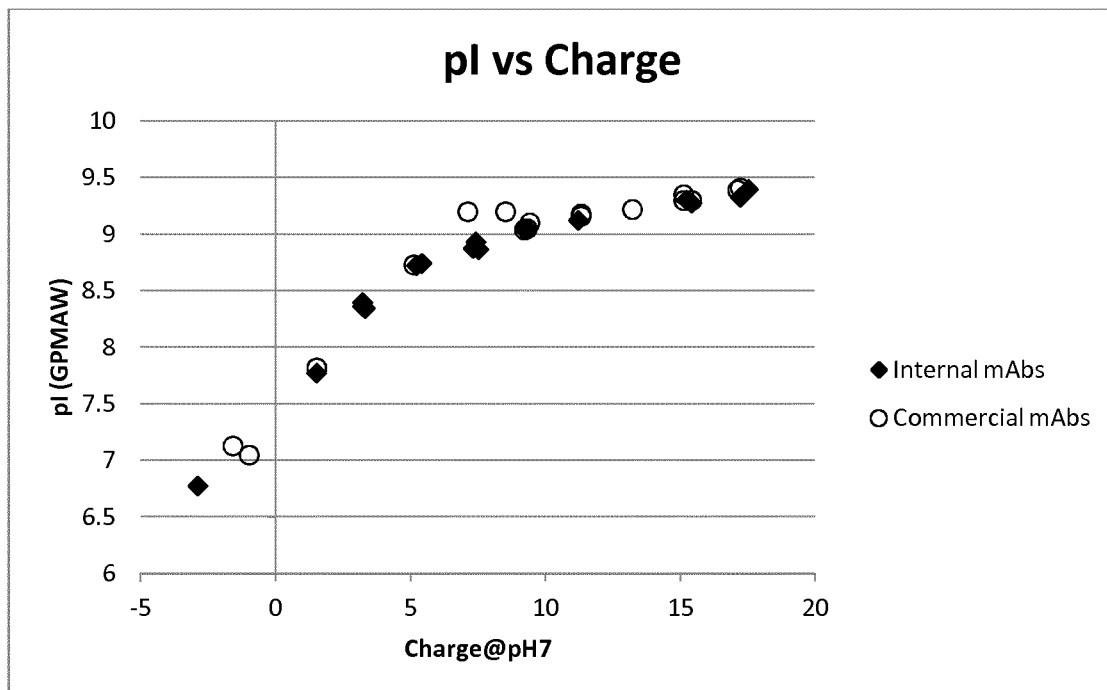

FIG. 7: Comparison of pI and charge at pH7, both calculated using GPMAW using internal and literature antibodies as a test set.

DETAILED DESCRIPTION OF THE INVENTION

The inventors have identified an unexpected correlation between bioavailability (BA) upon subcutaneous administration to a human and the net charge at around pH7 or the pI of an antibody therapeutic. This correlation is predictive of BA of an antibody upon subcutaneous administration in humans. Using this predictive correlation, it is possible to make, screen, select, modify, and engineer antibody sequences with improved BA upon subcutaneous administration to a human.

Improving the BA in this way could reduce the Active Pharmaceutical Ingredient (API) Cost of Goods (COGs). Furthermore, improving the BA in this way may also have an impact on the commercial viability of an antibody where the dose is such that the frequency or volume of injection would be too high, for example for the patient, or as compared with a competitor molecule; or the concentration would be too difficult to formulate due to viscosity issues.

The methods of the invention can result in an antibody with an improved BA. The improvement may be an improved predicted BA. The improved BA may be based on the correlations provided in the Examples. The methods of the invention can result in an antibody with a bioavailability of 60-100%; or 65-100%; or 70-100%; or 75-100%.

The antibody described herein may have a BA of at least 60%, at least 65%, at least 70%, at least 75%, at least 80%, at least 85%, at least 90%, or at least 95%. The BA values may be predicted BA values. The BA values may be based on subcutaneous administration of the antibody to a human.

"Bioavailability" (BA) is defined herein as the percentage of drug that reaches the systemic circulation. Bioavailability can be an estimate based on population PK modelling or based on subcutaneous dosing studies. Bioavailability may further be distinguished into the "absolute bioavailability" of a given dosage form as compared with that (100%) following intravenous administration (e.g. subcutaneous vs. intravenous), and the "relative bioavailability" as compared with another form administered by the same or another non-intravenous route (e.g. subcutaneous upper arm vs. subcutaneous thigh). For example, the improved BA described herein is an improved predicted BA, based on the correlations provided in the Examples.

"About" as used herein when referring to a measurable value such as an amount, a molecular weight, a temporal duration, and the like, is meant to encompass variations of ±1%, ±0.75%, ±0.5%, ±0.25%, ±0.2%, and ±0.1% from the specified value, as such variations are appropriate to perform the methods described.

As used herein, an "antibody" refers to IgG (such as IgG1, IgG2, IgG3 or IgG4), IgM, IgA, IgD or IgE antibodies; or a fragment thereof (such as a Fab, F(ab')2, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria. The antibody may be monoclonal, recombinant, polyclonal, chimeric (for example, from different sources (e.g. a human/mouse chimeric antibody) or different antibody types (e.g. an IgG2/4 antibody)), human, humanised, multispecific (including bispecific), or a heteroconjugate antibody.

The antibody may be an IgG1 antibody. The antibody may be a full length IgG antibody. The antibody may be a human or humanised or human-like antibody. The antibody may be a human or humanised or human-like IgG1 antibody. The antibody may be a monoclonal antibody. The antibody may be recombinant or synthetic. The light chain may be kappa light chain or the lambda light chain.

The antibody may not be an IgG1 Fc-fusion or an IgG1 Fab fragment. The antibody may not have an extreme charge distribution heterogeneity across the two IgG1 chains. The antibody may not formulated in the presence of hyaluronidase.

"CDRs" are defined as the complementarity determining regions on the antibody. There are three heavy chain and three light chain CDRs. Thus, "CDRs" as used herein refers to all three heavy chain CDRs, all three light chain CDRs, or all heavy and light chain CDRs.

Throughout this specification, amino acid residues in the antibody sequences are numbered according to the Kabat numbering convention.

"Net charge" is defined herein as the overall (global) charge of the antibody as determined from the amino acid sequence. There does not seem to be a predominant role for any particular region within the antibody, i.e., the Fc region, the Fv region, the CDRs, the light chain or the heavy chain, thus the net charge is a combination of the full sequence of the antibody. The net charge can be calculated using both the heavy and light chains of an antibody. For example, the net charge can be calculated using the entire antibody sequence, including the C-terminal lysine. Additionally, pI can be calculated using both the heavy and light chains of an antibody. For example, the pI can be calculated using the entire antibody sequence, including the C-terminal lysine. C-terminal lysines are commonly clipped/removed during manufacture or storage of the antibody drug product prior to administration or upon administration. If the C-terminal lysines are excluded from the antibody sequence (for example if the drug product deliberately does not contain the C-terminal lysines), then the net charge will be "x" minus 2.

The net charge can be calculated manually using the following equation:

Charge at pH7.0=(1×no. Asp)+(1×no. Glu)−(1×no. Lys)−(1×no. Arg)−(0.05×no. His).

The net charge can be calculated using GPMAW (General Protein/Mass Analysis for Windows). Alternatively, net charge can be calculated using EMBOSS (European Molecular Biology Open Software Suite) pepstats (K, R=+1.0; H=+0.5; D, E=−1.0). EMBOSS pepstats uses the same equation as GPMAW but sets His=0.5 (default parameters). Excluding the His contribution (i.e. His=0) provides values closer to that generated by GPMAW.

Net charge at different pHs can be determined by adjusting the charge on His and on Asp/Glu residues at the different pHs. For example, net charge can be calculated at pH2, pH5, pH6, and/or pH7 by a skilled person.

The net charge of the antibody sequence can be calculated at about pH7. It will be understood that as used herein, "about pH7" refers to an approximate value, therefore may refer to a pH range of 6.6 to 7.4, 6.7 to 7.3, 6.8 to 7.2, 6.9 to 7.1. The inventors have found that net charge at this pH range best correlates with BA. pH7 is also the most physiologically relevant in the SC environment, which is around 7.1-7.4. For example, the net charge of the antibody sequence is calculated at pH7 using a computational program. The computational method used to calculate net charge may be GPMAW. The use of net charge at about pH7 may be a more reliable predictor of BA, than the use of pI.

Charged amino acids are defined herein as below in Table 1. All other natural amino acids are classed as neutral.

TABLE 1

Summary of charged amino acids

| Charge | Amino acid | 3-letter code | 1-letter code |
|---|---|---|---|
| Positive | Arginine | Arg | R |
| | Histidine | His | H |
| | Lysine | Lys | L |
| Negative | Aspartic acid | Asp | D |
| | Glutamic acid | Glu | E |

"pI" is the pH at which the net charge on the protein is zero. This may be calculated by a variety of methods, for example experimentally or computationally. For example, pI can be calculated from the protein sequence using the pKa values of charged residues. The "experimental pI" is determined experimentally, for example by using isoelectric focusing. Isoelectric focussing can be performed in various ways, such as using a gel based method or using capillary IEF. When a computational method is used, the pI can be calculated by taking into account pKa values of Asp, Glu, Lys, Arg, and His residues but also Cys and Tyr, as well as the N- and C-terminal residues. There are several programs available for calculating pI, for example, GPMAW, EMBOSS pepstats and EMBOSS iep. GPMAW uses three different methods and quotes pI values from all three. An average of the three GPMAW pI values can be used. The exact equations used, as well as the pKa values, vary across the three programs.

The computational method used to calculate pI may be GPMAW, EMBOSS pepstats or EMBOSS iep. pI can be calculated using GPMAW (average) or iep. For example, GPMAW (average) is used to calculate pI. The pI value may be calculated using any computational method that correlates with experimental pI.

"pKa" is the $-\log_{10}$ of the acid dissociation constant (also known as the acidity constant or acid-ionisation constant) or the equilibrium constant of the dissociation reaction of an acid, which is a quantitative measure of the acidic strength of a molecule in solution.

The methods described herein allow for tuning the overall antibody charge or pI of an antibody to improve bioavailability. The present inventors have surprisingly found that tuning the global charge or pI of the antibody within the values described herein can result in improved bioavailability. Described herein is a method of charge tuning an IgG1 comprising selecting, screening, engineering, making and modifying the IgG to result in a net charge at about pH7 that is closer to +5; and/or a net charge of between 0 and +12 calculated at about pH7.

Using the net charge and pI values described herein, an antibody, a variant antibody, or an antibody sequence library, can be selected, made, or modified to result in an antibody with improved BA. The amino acid sequence of the antibody may be selected, combined, engineered, made, or modified, in order to improve the bioavailability.

The net charge of the antibody may be between 0 and +12 at about pH7 to ensure adequate bioavailability by subcutaneous administration to a human. The net charge may be between 0 to +10, or 0 to +8, or 0 to +5. For example, the net charge is between +1 to +12, or +1 to +10, or +1 to +8, or +1 to +5. Alternatively, the net charge of the antibody is between +4 to +12, or +4 to +10, or +4 to +8, or +4 to +6. The inventors have found that high bioavailability is associated with antibodies with a net charge of about +5.

The pI of the antibody may be between 8.4 and 9.3 to ensure adequate bioavailability by subcutaneous administration to a human. For example, the pI is between 8.5 to 9.3, or 8.5 to 9.25, or 8.5 to 9.2. Alternatively, the pI of the antibody is between 8.6 to 9.3, or 8.6 to 9.25, or 8.6 to 9.2, or 8.6 to 9.1, or 8.6 to 9.0. The pI may be between 8.7 and 9.1, or 8.7 and 9.0, or 8.7 and 8.9. The inventors have found that high bioavailability is associated with antibodies with a pI of about 8.8.

Described herein is a method of selecting an antibody comprising: (a) producing two or more antibodies to the same antigen; and (b) selecting the antibody sequence which has:

(i) a net charge at about pH7 that is closer to +5, or a pI that is closer to 8.8; and/or (ii) a net charge of between 0 and +12 at about pH7, or a pI of between 8.4 and 9.3. The antibody selected is distinguished from the other antibodies because the net charge or pI of the antibody is within the values described herein, and the antibody selected has a bioavailability that is greater than the other antibodies. For example, the method involves selecting an antibody with improved bioavailability for subcutaneous administration to a human.

Described herein is a method of making an antibody which comprises selecting and combining two or more human germline framework sequences, regions, or amino acids, to generate an antibody which has: a net charge of between 0 and +12 at about pH7, or a pI of between 8.4 and 9.3.

Also described is a method of de novo antibody design which comprises combining two or more human germline framework sequences, regions, or amino acids, to generate a chimeric antibody which has: (i) a net charge of between 0 and +12 at about pH7.0 or (ii) a pI of between 8.4 and 9.3.

The combination of two or more human germline framework sequences in the methods and variant antibodies described herein may involve an entire framework variable or constant sequence, a framework region or a framework amino acid. The combination involves amino acid(s) from different human antibody germline sequences.

The amino acid sequence of the antibody may be combined, engineered, or modified, in order to improve the bioavailability. The amino acid may be a naturally occurring amino acid from another human antibody sequence, e.g. another human germline sequence. Thus, the risk of an immunogenic response upon administration to humans may be diminished.

In particular, combining, engineering, or modifying, the framework regions or constant regions is described. For example, the complementarity determining region (CDR) is not changed. Thus any antibody sequence changes will have no or little impact on antigen binding. For example, the antibody retains its antigen-binding activity.

Described herein is a method of improving the bioavailability of an antibody which is subcutaneously administered to a human, comprising modifying the amino acid sequence of the antibody to result in: a net charge of between 0 and +12 at about pH7, or a pI of between 8.4 and 9.3.

The modification may comprise making one or more amino acid substitutions; or at least one amino acid substitution. The substitution may be in a region selected from, the Fc or the Fv region. The substitution may be in the Fv region. For example, the substitution is in Framework 1, Framework 2, Framework 3, and/or Framework 4. In particular, the substitution is not in the CDR.

For example, the substitution is on the heavy chain. Alternatively, the substitution is on the light chain. Alternatively, there are at least two amino acid substitutions, which may be on the same chain (heavy or light) or on different chains (heavy and light).

There may be at least 1, 2, 3, 4, 5, 6, 7, 8, 9 or 10 amino acid substitutions per antibody.

The substitution may be to a different amino acid and selected from another human antibody germline sequence.

Described herein is a variant antibody which is a variant of a parent antibody sequence, wherein the variant comprises combining two or more human germline framework sequences, regions, or amino acids. The variant is distinguished from the parent because the net charge or pI of the antibody is within the values described herein. The variant has a bioavailability that is greater than the parent antibody.

The antibody selected by the methods described herein, or the variant antibody described herein has a net charge difference between 1 and 20, such as 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3 or 1 to 2, when compared to the other antibody sequence. Alternatively, the antibody has a net charge difference between 1 and 4, such as 1 to 2, when compared to the other antibody sequence. The antibody may have a net charge difference of 1 (e.g. positive to neutral, or negative to neutral, or vice versa) when compared to the other antibody sequence. It will be understood by the person skilled in the art that the net charge difference may have an overall positive or negative charge difference (i.e., +1 or −1, +2 or −2, +3 or −3, +4 or −4 etc.) depending on the amino acid substitutions made.

The amino acid from a different human germline sequence, may be selected, engineered, combined, modified or substituted based on a residue wherein:

(a) a positive amino acid is changed to a neutral or negative amino acid;
(b) a negative amino acid is changed to a neutral or positive amino acid; or
(c) a neutral amino acid is changed to a positive or negative amino acid.

The amino acid selected, engineered, combined, modified or substituted may be at any one or a combination of Kabat residues selected from: H1, H6, H12, H13, H16, H19, H23, H43, H75, H81, H83, H85, L17, L18, L42, L74, L77, or L79. The amino acid substitution may be at any one or a combination of Kabat residues selected from: H6, H12, H13, H16, H19, H23, H43, H75, H81, H83, H85, L17, L18, L42, L74, L77, or L79. The amino acid substitution may be at any one or a combination of Kabat residues selected from: H6, H12, H13, H16, H19, H23, H43, H75, H85, L17, L18, L42, L74, L77, or L79. The amino acid substitution may be at any one or a combination of Kabat residues selected from: H12, H16, H19, H43, H75, L17, L18, L74, or L79. The amino acid substitution may be at any one or a combination of Kabat residues selected from: H12, H16, H43, H75, L17, L18, or L74.

The amino acid selected, combined, modified or substituted may be at any one or a combination of Kabat residues selected from: H1, H6, H12, H19, H75, L17, L42, L74, L77 or L79. The amino acid substitution may be at any one or a combination of Kabat residues selected from: H6, H12, H75, L42, L74, L77, or L79. The amino acid substitution may be at any one or a combination of Kabat residues selected from: H12, H75, L74, or L79.

The amino acid selected, combined, modified or substituted may be:
(a) a neutral or negative amino acid at H1, H6, H85, or L17;
(b) a neutral or positive amino acid at H12, H19, H23, H75, H83, L18, L42, L74, or L77; or
(c) a neutral or negative or positive amino acid at H13, H16, H43, H81, or L79.

The amino acid substitution may be:
(a) a neutral or negative amino acid at H1, H6, or L17;
(b) a neutral or positive amino acid at H12, H19, H75, L42, L74, or L77; or
(c) a neutral or negative or positive amino acid at L79.

Examples of the possible amino acid changes at particular Kabat residues are summarised in Table 2, below. It will be understood by a person skilled in the art that any one or a combination of the amino acid changes discussed above and in Table 2 may be made to the antibodies, variants, libraries or in the methods encompassed by the present invention.

TABLE 2

Examples of amino acid changes at particular Kabat residues within the antibody heavy or light chain.

| | | Substitution to −1 charge | Substitution to −2 charges | Substitution to +1 charge | Substitution to +2 charges |
|---|---|---|---|---|---|
| Kabat Heavy Chain | | | | | |
| 1 | E/Q | | Q to E (neutral to −) | | E to Q (− to neutral) |
| 6 | E/Q | | Q to E (neutral to −) | | E to Q (− to neutral) |
| 12 | V/K | K to V (+ to neutral) | | V to K (neutral to +) | |

TABLE 2-continued

Examples of amino acid changes at particular Kabat residues within the antibody heavy or light chain.

| | | Substitution to −1 charge | Substitution to −2 charges | Substitution to +1 charge | Substitution to +2 charges |
|---|---|---|---|---|---|
| 13 | K/Q/E | K to Q (+ to neutral) | K to E (+ to −) | Q to K (neutral to +) | E to K (− to +) |
| 16 | R/Q/A/G/S/E | Q/A/G/S to E (neutral to −) or R to Q/A/G/S (+ to neutral) | R to E (+ to −) | E to Q/A/G/S (− to neutral) or Q/A/G/S to R (neutral to +) | E to R (− to +) |
| 19 | R/S/K/T | R/K to S (+ to neutral) K/R to T (+ to neutral) | | S to R/K (neutral to +) T to K/R (neutral to +) | |
| 23 | A/K/T | K to A/T (+ to neutral) | | A/T to K (neutral to +) | |
| 43 | K/Q/R/E | K to Q (+ to neutral) Q to E (neutral to −) | R to E (+ to −) | Q to K (neutral to +) E to Q (− to neutral) | E to R (− to +) |
| 75 | K/T | K to T (+ to neutral) | | T to K (neutral to +) | |
| 81 | E/K/Q/R | Q to E (neutral to −) K/R to Q (+ to neutral) | K to E (+ to −) | E to Q (− to neutral) Q to K/R (neutral to +) | E to K (− to +) |
| 83 | R/T | R to T (+ to neutral) | | T to R (neutral to +) | |
| 85 | A/E | A to E (neutral to −) | | E to A (− to neutral) | |
| Kabat Light Chain | | | | | |
| 17 | E/D/Q | Q to E/D (neutral to −) | | E/D to Q (− to neutral) | |
| 18 | R/P/S | R to P/S (+ to neutral) | | P/S to R (neutral to +) | |
| 42 | K/Q | K to Q (+ to neutral) | | Q to K (neutral to +) | |
| 74 | K/T | K to T (+ to neutral) | | T to K (neutral to +) | |
| 77 | R/S | R to S (+ to neutral) | | S to R (neutral to +) | |
| 79 | Q/E/K/T | Q to E (neutral to −) K to T (+ to neutral) | | E to Q (− to neutral) T to K (neutral to +) | |

For example any one or a combination of the following substitutions can be made in a single antibody:

H12: V to K (neutral to positive=+1 charge)
H16: A/G/S to E (neutral to negative=−1 charge)
H19: R to S (positive to neutral=−1 charge)
H43: K to Q (positive to neutral=−1 charge)
H75: K to T (positive to neutral=−1 charge) or T to K (neutral to positive=+1 charge)
L17: E/D to Q (negative to neutral=+1 charge)
L18: R to P/S (positive to neutral=−1 charge)
L74: K to T (positive to neutral=−1 charge)
L79: Q to E (neutral to negative=−1 charge).

It will be understood by a person skilled in the art that if the amino acid changes suggested herein are made to an antibody, then the total charge change will be doubled because the amino acid change is made on both of the heavy or light chains of the antibody molecule, e.g. a change at position H12 of V to K (i.e. neutral to positive=+1 charge) would result in a +2 charge change to the overall antibody charge because this change would be made on both heavy chains.

Described herein is a method of making an antibody sequence library, wherein the library is engineered to comprise antibodies having a net charge of between 0 and +12 at about pH7, or a pI of between 8.4 and 9.3. Also described is a method of making an antibody which comprises isolating an antibody from the antibody sequence library.

It will be understood that the method of making the antibody sequence library may comprise amino acid framework residues to ensure that an antibody derived from the library have the net charge and/or pI values described herein. For example, the library may have fixed amino acid positions as discussed hereinbefore (e.g. see the changes discussed in Table 2, above).

The following framework sequences may achieve a net charge of between 0 and +12 at about pH7.0, or pI of between 8.4 and 9.3 in the antibody sequence library:

(a) a neutral or negative amino acid at H1, H6, H85, L3, or L17;

(b) a neutral or positive amino acid at H12, H19, H23, H75, H83, L18, L42, L74, or L77; or (c) a neutral or negative or positive amino acid at H13, H16, H43, H81, or L79.

The term "library" refers to a mixture of heterogeneous polypeptides or nucleic acids. The library is composed of members, each of which has a single polypeptide or nucleic acid sequence. To this extent, "library" is synonymous with "repertoire". Sequence differences between library members are responsible for the diversity present in the library. The library may take the form of a simple mixture of polypeptides or nucleic acids, or may be in the form of organisms or cells, for example bacteria, viruses, animal or plant cells, transformed with a library of nucleic acids. In one example, each individual organism or cell contains only one or a limited number of library members. The nucleic acids may be incorporated into expression vectors, in order to allow expression of the polypeptides encoded by the nucleic acids. A library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides. The library may be a phage (e.g. a bacteriophage), yeast or ribosome library.

Described herein is a variant of a parent human antibody sequence, wherein the variant comprises combining two or more human germline framework sequences, regions or amino acids to generate a variant antibody having: (i) a net charge at about pH7.0 that is closer to +5 or a pI closer to 8.8 than the parent antibody sequence; and/or (ii) a net charge of between 0 and +12 at about pH7 or a pI of between 8.4 and 9.3 compared with the parent antibody sequence. The parent antibody may be modified in the same way as discussed hereinbefore to produce a variant of the parent antibody sequence. For example, the amino acid substitution is in the Fv region. The amino acid substitution may not be in the complementarity determining region (CDR). The variant may have a net charge difference between 1 and 4 when compared to the parent antibody sequence. The amino acid substitution may: (a) change a positive amino acid to a neutral or negative amino acid; (b) change a negative amino acid to a neutral or positive amino acid; or (c) change a neutral amino acid to a positive or negative amino acid. In one embodiment, the amino acid substitution is at any one or a combination of Kabat residues selected from: H1, H6, H12, H13, H16, H19, H23, H43, H75, H81, H83, H85, L17, L18, L42, L74, L77, or L79. The amino acid substitution may be at any one or a combination of Kabat residues selected from: H12, H16, H19, H43, H75, L17, L18, L74, or L79.

The net charge of the variant antibody may be between 0 and +12 at about pH7 to ensure adequate bioavailability by subcutaneous administration to a human. The net charge may be between 0 to +10, or 0 to +8, or 0 to +5. For example, the net charge is between +1 to +12, or +1 to +10, or +1 to +8, or +1 to +5. Alternatively, the net charge of the antibody is between +4 to +12, or +4 to +10, or +4 to +8, or +4 to +6. The inventors have found that high bioavailability is associated with antibodies with a net charge of about +5.

The pI of the variant antibody may be between 8.4 and 9.3 to ensure adequate bioavailability by subcutaneous administration to a human. For example, the pI is between 8.5 to 9.3, or 8.5 to 9.25, or 8.5 to 9.2. Alternatively, the pI of the antibody is between 8.6 to 9.3, or 8.6 to 9.25, or 8.6 to 9.2, or 8.6 to 9.1, or 8.6 to 9.0. The pI may be between 8.7 and 9.1, or 8.7 and 9.0, or 8.7 and 8.9. The inventors have found that high bioavailability is associated with antibodies with a pI of about 8.8.

The net charge may be calculated using the entire antibody sequence, including the C-terminal lysine. For example the variant retains its antigen-binding activity. The variant may be an IgG1 antibody.

The antibodies described herein (made, selected, modified, variants, resulting from the methods) have an improved BA, for example a predicted BA based on the correlations provided in the Examples. The antibody may have a bioavailability of 60-100%; or 65-100%; or 70-100%; or 75-100%. The antibody may have a BA of at least 60%, at least 65%, at least 70%, at least 75%, at least 80%, at least 85%, at least 90%, or at least 95%.

The invention will now be explained in more detail with reference to the following Examples.

EXAMPLES

The following examples are included to demonstrate the correlation between charge or pI and bioavailability upon subcutaneous delivery to a human, and provide support for a method of increasing the predicted bioavailability of an antibody.

Example 1—Human Bioavailability Values

Twenty antibodies were identified from the literature or in-house portfolio as being administered by subcutaneous injection. These are listed in Table 3. The bioavailability of these antibodies ranges from 43-87%.

TABLE 3

Bioavailability data for commercial antibody sequences, and internal antibodies.

| Product | Generic Name | Ab format | Target/MoA | Reference | Human SC BA (%) |
|---|---|---|---|---|---|
| mAb1 | | Human IgG1 | | In-house | 87 |
| Cimzia ™ | Certolizumab pegol | Pegylated Humanised Fab Fragment | TNF-α | McDonald | 82 |
| Herceptin ™ | Trastuzumab | Humanised IgG1 | HER2 | EMA | 82 |
| | Tralokinumab | Human IgG4 | IL13 | Baverel | 82 |
| Orencia ™ | Abtacept | CTLA-4 Fc (IgG1) fusion | CD80/86 | EMA | 79 |
| Prolia ™ | Denosumab | Human IgG2 | RANKL | EMA | 78 |
| Benlysta ™ | Belimumab | Human IgG1 | BLγS | Cai | 76 |
| Enbrel ™ | Etanercept | TNFR-Fc (IgG1) fusion | TNF-α | EMA | 76 |
| mAb2 | | Humanised IgG1 | | In-house | 75 |
| mAb3 | | Humanised IgG1 | | In-house | 75 |
| Mabthera ™ | Rituximab | Mouse/human chimeric IgG1 | CD20 | EMA | 71 |

TABLE 3-continued

Bioavailability data for commercial antibody sequences, and internal antibodies.

| Product | Generic Name | Ab format | Target/MoA | Reference | Human SC BA (%) |
|---|---|---|---|---|---|
| Ilaris ™ | Canakinumab | Human IgG1 | IL-1β | EMA | 66 |
| Humira ™ | Adalimumab | Human IgG1 | TNF-α | EMA | 64 |
| Xolair ™ | Omalizumab | Humanised IgG1 | IgE | EMA | 62 |
| Stelara ™ | Ustekinumab | Human IgG1 | p40 (IL-12/23) | EMA | 57 |
| Actemra ™ | Tocilizumab | Humanised IgG1 | IL-6R | EMA | 53 (80) |
| mAb4 | | Human IgG1 | | In-house | 52 |
| Simponi ™ | Golimumab | Human IgG1 | TNF-α | EMA | 51 |
| Raptiva ™ | Efalizumab | Humanised IgG1 | CD11a | EMA | 50 |
| Arcalyst ™ | Rilonacept | ILRAP-ILR1-Fc (IgG1) | IL-1-beta | EMA | 50 |

EMA: European Medicines Agency
For Tocilizumab, a BA of 53% was used in place of the EMA predicted value of 80%. This is discussed in Example 2.
References: McDonald et al. (2010) *Curr. Opin. Mol. Ther.* 2 (4), p. 461-70; Cai et al. (2013) *Clin. Pharmacol. Drug Dev.* 2 (4), p. 349-357; Baverel et al. (2012) *Eur. Resp. J.* 40 (Suppl 56): P2340

Example 2—Human Bioavailability Correlations

Preliminary analysis on molecular weight and dose showed no obvious correlations to explain the wide ranging values of BA. Fourteen of the full length antibodies were examined by sequence aligning the V and C regions using GeneDoc software. No obvious sequence features could be identified as being responsible for the variation in bioavailability.

Further sequence properties were then evaluated. Net charge was calculated using GPMAW (at pH 2.0, 5.0 and 7.0, i.e. adjusting the charge on His and on Asp/Glu at the different pHs). pI was calculated using EMBOSS iep and GPMAW. Both iep and GPMAW can calculate the pI of the protein in a reduced (-SH) and non-reduced (-SS) state. GPMAW also calculates the pI using three different methods, and thus a mean was generated across the methods.

These property values were then correlated against bioavailability values, as shown in Table 4 and FIG. 1.

TABLE 4

Net charge and pI correlations against bioavailability values for individual antibody sequences

| Ab | Format | SC BA (%) | Net Charge @ pH 2.0 (GPMAW) | Net Charge @ pH 5.0 (GPMAW) | Net Charge @ pH 7.0 (GPMAW) | Mean pI (GPMAW-SS) | pI (iep) |
|---|---|---|---|---|---|---|---|
| mAb1 | IgG1 | 87 | 142.3 | 33.5 | 5.1 | 8.73 | 8.88 |
| *Cimzia ™ (certolizumab pegol)* | Fab | 82 | 42.3 | 11 | 4.3 | 9.16 | 9.09 |
| *Herceptin ™ (trastuzumab)* | IgG1 | 82 | 154.3 | 43.1 | 11.3 | 9.15 | 9.24 |
| *Tralokinumab* | IgG4 | 82 | 140.7 | 26 | -1 | 7.05 | 8.06 |
| *Orencia ™ (abatacept)* | Fc fusion | 79 | 84.7 | 9 | -11.2 | 5.83 | 6.22 |
| *Prolia ™ (denosumab)* | IgG2 | 78 | 148.3 | 36 | 9 | 9.12 | 9.22 |
| Benlysta ™ (belimumab) | IgG1 | 76 | 150.7 | 43.1 | 9.4 | 9.10 | 9.21 |
| *Enbrel ™ (etanercept)* | Fc fusion | 76 | 114.7 | 27.8 | 1.1 | 7.87 | 8.32 |
| mAb2 | IgG1 | 75 | 148.3 | 39.4 | 9.2 | 9.04 | 9.15 |
| mAb3 | IgG1 | 75 | 154.3 | 43.1 | 11.3 | 9.18 | 9.29 |
| *Mabthera ™ (rituximab)* | IgG1 | 71 | 152.3 | 50.7 | 19.3 | 9.41 | 9.51 |
| Ilaris ™ (canakinumab) | IgG1 | 66 | 156.3 | 41.4 | 9.3 | 9.05 | 9.17 |
| Humira ™ (adalimumab) | IgG1 | 64 | 156.3 | 43.2 | 11.3 | 9.16 | 9.25 |
| *Xolair ™ (omalizumab)* | IgG1 | 62 | 154.3 | 37.4 | 1.5 | 7.82 | 8.43 |
| Stelara ™ (ustekinumab) | IgG1 | 57 | 152.3 | 43.1 | 15.1 | 9.31 | 9.40 |
| Actemra ™ (tocilizumab) | IgG1 | 53 (80) | 152.3 | 48.5 | 17.3 | 9.33 | 9.48 |
| mAb4 | IgG1 | 52 | 148.7 | 45.3 | 17.1 | 9.39 | 9.48 |
| Simponi ™ (golimumab) | IgG1 | 51 | 156.3 | 45.2 | 15.2 | 9.22 | 9.39 |
| Raptiva ™ (efalizumab) | IgG1 | 50 | 160.3 | 49.3 | 15.4 | 9.30 | 9.38 |
| *Arcalyst ™ (rilonacept)* | Fc fusion | 50 | 254.8 | 55.5 | -3.6 | 6.95 | 7.41 |

TABLE 4-continued

Net charge and pI correlations against bioavailability values for individual antibody sequences

| Ab | Format | SC BA (%) | Net Charge @ pH 2.0 (GPMAW) | Net Charge @ pH 5.0 (GPMAW) | Net Charge @ pH 7.0 (GPMAW) | Mean pI (GPMAW-SS) | pI (iep) |
|---|---|---|---|---|---|---|---|
| Pearson (all) | | | −0.54 | −0.64 | −0.40 | −0.19 | −0.20 |
| Pearson (excluding others) | | | −0.61 | −0.85 | −0.93 | −0.87 | −0.89 |

*Asterisk marks "others" that are excluded from "Pearson (excluding others)", "others" include abtacept, etanercept, rilonacept, certolizumab, denosumab, tralokinumab, omalizumab, rituximab and trastuzumab and reasons for exclusion are explained below.

If all of the antibodies are included in the analysis a correlation is observed with the GPMAW net charge calculations at pHs 2.0 and 5.0 (see "Pearson (all)"). From the graphs, the low correlations seen with the other parameters are primarily due to data-points with low net charge values (see FIG. 1). Upon inspection, these appear to be primarily made up of non-IgG1 antibodies.

Differentiating the data by molecule format to focus on IgG1 antibodies, and to exclude those IgG1s with an extreme charge distribution heterogeneity across the molecule, and those formulated in the presence of hyaluronidase (which independently improves BA), it becomes clear that there is a strong correlation with subcutaneous bioavailability (see FIG. 2) and a Pearson correlation of −0.93 in Table 4 "Pearson (excluding others)".

FIG. 2 "IgG1" includes: mAb1, belimumab, mAb2, mAb3, canakinumab, adalimumab, ustekinumab, tocilizumab, mAb4, golimumab, and efalizumab. The "others" are made up of non-full-length IgG1: Fc-fusions (abtacept, etanercept, rilonacept), a Fab fragment (certolizumab); IgG2 (denosumab); IgG4 (tralokinumab); omalizumab, which is an IgG1, but is unusual in that it has an extreme charge distribution heterogeneity across the molecule (also the antigen for Xolair is IgE and therefore target binding might impact bioavailability), and rituximab and trastuzumab which are formulated in the presence of hyaluronidase (see information on Rituximab™ and Herceptin™ on the EMA website and as described in Shpilberg and Jackisch (2013) Br. J. Cancer, 109(6), 1556-1561).

It is noted that the "Pearson Correlation" is a term well known in the art which refers to a measure of the linear dependence between two variables X and Y, giving a value between +1 and −1 inclusive, where +1 is total positive correlation, 0 is no correlation, and −1 is total negative correlation.

Note that the European Medicines Agency (EMA) report for Actemra™/tocilizumab provides a BA of 80% which is an estimate based upon population PK modelling (see the EMA assessment for Actemra™/RoActemra™), and is substantially higher than the 48.8% and 56.5% observed in previously reported single dose studies (see Zhang et al. (2013) Int. J. Gin. Pharmacol. Ther. 51(6), p. 443-55). The average of the lower values (53%) more closely fits on the line of correlation than the estimated value (see FIG. 3). The average value is provided in Tables 3, 4, and in FIGS. 1 and 2.

The data indicates that pH7 is the optimum pH for calculating charge. Below this pH the Pearson correlation decreases. The optimum charge at pH7, for maximum bioavailability, appears to be around +5, or between 0 and +12. It is difficult to predict the effect of charge at 7 below +5 because of the "others" in FIG. 2a. The optimum charge may actually be between 0 to +5, or from +1 to +5.

The data also indicates that the optimum pI for maximum bioavailability appears to be around 8.8, or between 8.4 and 9.3. It is difficult to predict the effect of pI below 8.8 because of the "others" in FIG. 2b. The optimum pI may actually be between 8.4 and 8.8.

Comparing the charge and pI data suggests that while both show a correlation, the correlation is better for the charge at pH7 data. This is reinforced when using $R^2$ values for the same dataset, which show a correlation of 0.89 for charge at pH7 and 0.73 for pI (calculated by GPMAW). "$R^2$" refers to the square of the correlation coefficient which is a measure of the degree of correlation between two variables.

The strong correlation observed between human bioavailability data and net charge or pI does not translate to non-human models. Plotting *Cynomolgus* monkey data (obtained from Richter et al. (2012) AAPS J. 14(3), 559-570) for the four IgGs: Canakinumab, Adalimumab, Golimumab, Ustekinumab; and "others" including the non-IgGs Etanercept, and Rilanocept, and the IgG1 Omalizumab (having extreme charge heterogeneity) listed in Table 3; against their net charge at pH7 does not result in any obvious correlation (see FIG. 4). In contrast, there is a clear correlation for these four IgGs for human BA and net charge or pI.

Example 3—Analysis of the Relationship Between pI and Charge

The present inventors have surprisingly found that using net charge at about pH7 and/or pI is a good predictor of human bioavailability upon subcutaneous delivery. This is explained in more detail, below.

Both net charge and pI can be calculated from the sequence of a protein. "Net charge" is the overall charge of a protein based upon summing the contributions from charged residues at a particular pH. Therefore the charge will vary dependent upon the pH.

At about pH 7 (closest to the interstitial space, where SC drugs are injected), the net charge is calculated by GPMAW using the following equation:

Charge at pH7.0=(1×no. Asp)+(1×no. Glu)−(1×no. Lys)−(1×no. Arg)−(0.05×no. His)

EMBOSS pepstats uses the same equation but sets His=0.5 (default parameters). Excluding the His contribution (i.e. His=0) provides values closer to that generated by GPMAW.

"pI" is the pH at which the net charge on the protein is zero. This may be calculated by a variety of methods from the protein sequence, using the pKa values of charged residues. The pI can be calculated by taking into account pKa values of Asp, Glu, Lys, Arg, and His residues but also Cys and Tyr, as well as the N- and C-terminal residues.

The inventors have used three different programs, GPMAW, EMBOSS pepstats and EMBOSS iep to calculate pI. Both EMBOSS iep and GPMAW account for the disulfide bond status of the molecules. The exact equations used, as well as the pKa values, vary across the three programs. GPMAW uses three different methods and quotes pI values from all three. The variation in the pKa values used is summarised in Table 5.

TABLE 5 pKa values used in different programs to calculate pI

| Residue | GPMAW 1[a] | GPMAW 2[b] | GPMAW 3[c] | GPMAW Av | EMBOSS Iep and pepstats |
|---|---|---|---|---|---|
| Asp | 3.9 | 3.82 | 3.5 | 3.7 | 3.9 |
| Glu | 4.3 | 4.18 | 4.5 | 4.3 | 4.1 |
| Cys | 8.3 | 8.26 | 10.3 | 9.0 | 8.5 |
| Tyr | 10.1 | 10.11 | 10.3 | 10.2 | 10.1 |
| Lys | 10.5 | 10.66 | 10.3 | 10.5 | 10.8 |
| His | 6 | 6.08 | 6.2 | 6.1 | 6.5 |
| Arg | 12.5 | 12.48 | 12.5 | 12.5 | 12.5 |

[a]GPMAW 1 -from Skoog & Wichman (1986) *Trends Anal. Chem.*, 3, 82-83, [C(pos) = 1/(1 + a), where a = $10^{(pHtest-pKa)}$; C(neg) = a/(1 + a)]
[b]GPMAW 2 - from free amino acids
[c]GPMAW 3 - from Rickard et al. (1991) *Anal. Biochem.*, 197 (1), 197-207

The differences in residue pKa values leads to some variation in calculated pI values using three programs, as illustrated by FIG. 5 for the 16 antibodies from the literature (certolizumab, trastuzumab, tralokinumab, abtacept, denosumab, beliumumab, etanercept, rituximab, canakinumab, adalimumab, omalizumab, ustekinumab, tocilizumab, golimumab, efalizumab, and rilonacept.

Some computational methods more closely correlate with experimental data than others. The inventors have observed that pI calculations from GPMAW and EMBOSS iep closely correlate with in-house experimental data for in-house mAbs 2, 5 to 23 (see FIG. 6 and Table 6). However, it will be understood that any suitable computational method that can calculate pI that corresponds with experimental pI may be used.

TABLE 6

Experimental and predicted pI data of in-house mAbs

| mAb | Experimental pI | GPMAW 1 | GPMAW 2 | GPMAW 3 | pI Av GPMAW | iep pI |
|---|---|---|---|---|---|---|
| mAb5 | 7.52 | 8.37 | 8.42 | 8.25 | 8.35 | 8.65 |
| mAb6 | 7.7 | 8.73 | 8.80 | 8.64 | 8.72 | 8.91 |
| mAb7 | 7.86 | | | | | 8.97 |
| mAb8 | 8.06 | 8.42 | 8.48 | 8.29 | 8.40 | 8.70 |
| mAb9 | 8.22 | 8.93 | 8.98 | 8.88 | 8.93 | 9.04 |
| mAb10 | 8.3 | 8.87 | 8.93 | 8.83 | 8.88 | 9.00 |
| mAb11 | 8.54 | 9.04 | 9.09 | 9.00 | 9.04 | 9.14 |
| mAb12 | 8.67 | 8.93 | 9.00 | 8.87 | 8.93 | 9.06 |
| mAb13 | 8.71 | 9.11 | 9.17 | 9.09 | 9.12 | 9.22 |
| mAb14 | 9.05 | 9.31 | 9.37 | 9.30 | 9.33 | 9.42 |
| mAb15 | 9.16 | | | | | 9.47 |
| mAb16 | 9.18 | 9.38 | 9.46 | 9.35 | 9.40 | 9.51 |
| mAb17 | 9.23 | 9.29 | 9.36 | 9.26 | 9.30 | 9.41 |
| mAb2 | | 9.03 | 9.09 | 9.01 | 9.04 | 9.15 |
| mAb18 | | 8.39 | 8.45 | 8.25 | 8.36 | 8.67 |
| mAb19 | | 7.77 | 7.83 | 7.72 | 7.77 | 8.42 |
| mAb20 | 8.23 | 8.86 | 8.92 | 8.82 | 8.87 | 9.00 |
| mAb21 | 8.31 | 8.75 | 8.8 | 8.68 | 8.74 | 8.89 |
| mAb22 | | 6.7 | 6.76 | 6.87 | 6.78 | 7.61 |
| mAb23 | 8.96 | 9.26 | 9.33 | 9.24 | 9.28 | 9.37 |

TABLE 6-continued

Experimental and predicted pI data of in-house mAbs

| mAb | Experimental pI | GPMAW 1 | GPMAW 2 | GPMAW 3 | pI Av GPMAW | iep pI |
|---|---|---|---|---|---|---|
| Pearson correlation | | 0.92 | 0.92 | 0.91 | 0.92 | 0.93 |

Using GPMAW, it has been observed that the relationship between pI and charge is not linear (see FIG. 7). Using either internal or commercial Abs as a test set, above a charge of +5 the pI does not vary greatly (<1 pI unit between a charge of +5 and +17). However, it is in this region that we find the best correlation between charge and SC bioavailability. Below a charge of +5, the pI decreases rapidly with decreasing charge.

Thus the use of net charge at about pH7 may be a more reliable predictor of BA.

Example 4—Identifying Substitution Sites

The sequence of an antibody can be modified to improve the BA upon subcutaneous administration to a human. Fifteen antibodies were examined by sequence aligning the V and C regions using GeneDoc software.

The net charge was not attributable to specific regions (CDRs, frameworks or chains), but was found to be due to the combined sequence across both chains.

In addition to the V region, the C region could also be seen to be influential for the observed SC bioavailability, as evidenced by Tralokinumab and mAb1. These two antibodies have similar net charge across the V regions. However, Tralokinumab is a human IgG4 lambda1 antibody, whereas mAb1 is human IgG1 kappa, and the net charge of the C regions differ, IgG1 being positively charged as opposed to neutral for IgG4 (data not shown).

Neither the Fc nor the Fv region appears to play a predominant role in this correlation and the overall charge is important.

In silico sequence analysis was performed to identify potential positions within the conserved framework regions where charge could be modified with a germline-germline mutation. Specific residues were selected that could be used to adjust the antibody charge, as shown in Table 7.

TABLE 7

Potential residues to adjust antibody charge

| Kabat Position | Positive Mutation | Negative Mutation | Neutral Mutation |
|---|---|---|---|
| H1 | — | Glu | Gln |
| H6 | — | Glu | Gln |
| H12 | Lys | — | Val |
| H13 | Lys | — | Gln |
| H16 | Arg | Glu | Gly |
| H19 | Arg | — | Ser |
| H23 | Lys | — | Ala |
| H43 | Lys | — | Gln |
| H75 | Lys | — | Thr |
| H81 | Lys | Glu | Gln |
| H83 | Arg | — | Thr |
| H85 | — | Glu | Ala |
| L17 | — | Glu | Gln |
| L18 | Arg | — | Pro |
| L42 | Lys | — | Gln |
| L74 | Lys | — | Thr |

TABLE 7-continued

Potential residues to adjust antibody charge

| Kabat Position | Positive Mutation | Negative Mutation | Neutral Mutation |
|---|---|---|---|
| L77 | Arg | — | Ser |
| L79 | — | Glu | Gln |

The mutations shown in Table 7 were made individually across a set of human germline sequences, and potential immunogenicity risk was calculated in silico by predicting MHC class II T cell epitopes using TEpredict.

Example 5—Generating Mutants of Modified Net Charge

We can assess experimentally whether the mutation is 'benign' (i.e. no negative impact on the molecule e.g. on binding, titre, product quality, immunogenicity etc.).

In-house antibody sequences were aligned to identify suitable frameworks to assess the mutations. Each mutation was made in two different antibodies.

TABLE 8

Summary of mutations in selected antibodies

| mAb12 | mAb17 | mAb19 | mAb11 |
|---|---|---|---|
| WT | WT | WT | WT |
| V12K (HC) | T75K (HC) | T75K (HC) | V12K (HC) |
| K75T (HC) | A16E (HC) | S16E (HC) | K75T (HC) |
| G16E (HC) | K74T (LC) | E17Q (LC) | R19S (HC) |
| R19S (HC) | | K74T (LC) | K43Q (HC) |
| K43Q (HC) | | | D17Q (LC) |
| D17Q (LC) | | | R18P (LC) |
| R18P (LC) | | | Q79E (LC) |
| Q79E (LC) | | | |

Note that for each amino acid mutation, the total charge change will be doubled because the amino acid change is made on both of the heavy and/or both of the light chains of the antibody molecule, e.g. a change at position H12 of V to K (i.e. neutral to positive=+1 charge) would result in a +2 charge change to the overall antibody charge because this change would be made on both heavy chains.

These available substitution sites can be part of a toolbox during drug discovery to veneer or modify the antibody to improve the human subcutaneous BA. Alternatively, these different residues may be part of an antibody sequence library to ensure that the net charge is maximised for antibodies derived from the library.

REFERENCES

McDonald et al. (2010) Curr. Opin. Mol. Ther. 2(4), p. 461-70

Cai et al. (2013) Clin. Pharmacol. Drug Dev. 2(4), p. 349-357

Baverel et al. (2012) Eur. Resp. J. 40 (Suppl 56):P2340

Shpilberg and Jackisch (2013) Br. J. Cancer, 109(6), 1556-1561

Zhang et al. (2013) Int. J. Clin. Pharmacol. Ther. 51(6), p. 443-55

Richter et al. (2012) AAPS J. 14(3), 559-570

Skoog & Wichman (1986) Trends Anal. Chem., 3, 82-83

Rickard et al. (1991) Anal. Biochem. 197(1), 197-207

The invention claimed is:

1. A method of selecting an IgG1 antibody for subcutaneous administration to a human, comprising:
   (a) selecting the IgG1 antibody which has a net charge between +4 and +12 at a pH of 6.6 to 7.4; and
   (b) preparing a formulation comprising the selected IgG1 antibody without hyaluronidase, wherein the IgG1 antibody formulated has a bioavailability of at least 60% upon subcutaneous administration to a human.

2. The method of claim 1, wherein the net charge is calculated using the entire sequence of the IgG1 antibody, including a C-terminal lysine.

3. The method of claim 1, wherein there is a positive or negative or neutral amino acid at any one or a combination of Kabat residues H1, H6, H12, H13, H16, H19, H23, H43, H75, H81, H83, H85, L17, L18, L42, L74, L77, or L79 of the IgG1 antibody.

4. The method of claim 1, wherein the IgG1 antibody formulated has a bioavailability of at least 65%, at least 70%, or at least 75% upon subcutaneous administration to a human.

5. The method of claim 4 wherein said bioavailability is a predicted bioavailability.

6. The method of claim 1, wherein the net charge is between +4 and +10 at a pH of 6.6 to 7.4.

7. The method of claim 1, wherein the net charge is between +4 to +6 at a pH of 6.6 to 7.4.

* * * * *

UNITED STATES PATENT AND TRADEMARK OFFICE
CERTIFICATE OF CORRECTION

PATENT NO. : 11,203,632 B2
APPLICATION NO. : 15/749210
DATED : December 21, 2021
INVENTOR(S) : Damian et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 173 days.

Signed and Sealed this
Twenty-ninth Day of November, 2022

Katherine Kelly Vidal
*Director of the United States Patent and Trademark Office*